(12) United States Patent
DePuydt

(10) Patent No.: US 6,760,946 B2
(45) Date of Patent: Jul. 13, 2004

(54) BRUSH HEAD FOR TOOTHBRUSH

(75) Inventor: Joseph A. DePuydt, Quincy, MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 10/456,769

(22) Filed: Jun. 6, 2003

(65) Prior Publication Data
US 2003/0182747 A1 Oct. 2, 2003

Related U.S. Application Data

(63) Continuation of application No. 09/425,423, filed on Oct. 22, 1999, now Pat. No. 6,574,820.

(51) Int. Cl.$^7$ .............................................. A46B 13/02
(52) U.S. Cl. .............................. 15/22.4; 15/28; 15/22.1
(58) Field of Search ........................ 15/22.1, 28, 22.4, 15/29, 23, 22.2; 433/216

(56) References Cited

U.S. PATENT DOCUMENTS

| | | | |
|---|---|---|---|
| 2,140,307 A | | 12/1938 | Belaschk et al. ............ 15/28 |
| 3,129,449 A | | 4/1964 | Cyzer ........................... 15/28 |
| 3,270,360 A | * | 9/1966 | Kropp ......................... 15/22.1 |
| 3,732,589 A | | 5/1973 | Burki ......................... 15/22 R |
| 4,156,620 A | * | 5/1979 | Clemens ........................ 134/6 |
| 4,223,417 A | | 9/1980 | Solow ......................... 15/22 R |
| 4,320,774 A | | 3/1982 | Rogers ........................ 132/11 |
| 4,346,492 A | * | 8/1982 | Solow .......................... 15/22.1 |
| 4,545,087 A | * | 10/1985 | Nahum ........................ 15/22.1 |
| 4,766,630 A | * | 8/1988 | Hegemann .................. 15/21.1 |
| 4,845,795 A | * | 7/1989 | Crawford et al. ............ 15/22.1 |
| 5,027,463 A | | 7/1991 | Daub .......................... 15/22.1 |
| 5,068,939 A | * | 12/1991 | Holland ...................... 15/22.1 |
| 5,070,567 A | * | 12/1991 | Holland ........................ 15/28 |
| 5,088,145 A | * | 2/1992 | Whitefield .................. 15/22.1 |
| 5,138,734 A | * | 8/1992 | Chung .......................... 15/28 |
| 5,145,369 A | * | 9/1992 | Lustig et al. ................ 433/118 |
| 5,177,826 A | | 1/1993 | Vrignaud et al. ............. 15/22.1 |
| 5,184,368 A | * | 2/1993 | Holland ...................... 15/167.1 |
| 5,186,627 A | * | 2/1993 | Amit et al. .................. 433/216 |
| 5,226,206 A | | 7/1993 | Davidovitz et al. .......... 15/22.1 |
| 5,259,083 A | * | 11/1993 | Stansbury, Jr. ............... 15/22.1 |
| 5,276,932 A | | 1/1994 | Byrd ............................. 15/28 |
| 5,301,381 A | * | 4/1994 | Klupt .......................... 15/22.1 |
| 5,416,942 A | * | 5/1995 | Baldacci et al. ............. 15/22.1 |
| 5,446,939 A | * | 9/1995 | Park ............................... 15/23 |
| 5,450,646 A | * | 9/1995 | McHugh et al. ............. 15/22.1 |
| 5,499,420 A | * | 3/1996 | Boland ........................ 15/22.1 |
| 5,500,970 A | * | 3/1996 | Maurer et al. ............... 15/22.1 |
| 5,504,959 A | * | 4/1996 | Yukawa et al. .............. 15/22.1 |
| 5,524,312 A | * | 6/1996 | Tan et al. ..................... 15/22.1 |
| 5,546,626 A | * | 8/1996 | Chung ........................ 15/167.1 |
| 5,573,020 A | * | 11/1996 | Robinson .................... 132/322 |
| 5,577,285 A | * | 11/1996 | Drossler ..................... 15/22.1 |
| 5,617,603 A | | 4/1997 | Mei ............................. 15/22.1 |
| 5,625,916 A | * | 5/1997 | McDougall .................... 15/28 |

(List continued on next page.)

FOREIGN PATENT DOCUMENTS

| | | | | |
|---|---|---|---|---|
| DE | 29517610 | * | 4/1997 | |
| DE | 19803311 | * | 8/1999 | |
| EP | 0488971 A2 | | 11/1991 | ........... A61C/17/26 |
| JP | 10-66704 | * | 3/1998 | |
| TW | 135303 | | 6/1990 | |
| TW | 253174 | | 7/1994 | |
| TW | 330411 | | 4/1998 | |
| WO | WO 94/23667 | | 10/1994 | ........... A61C/17/34 |
| WO | WO 94/28823 | | 12/1994 | ........... A61C/17/40 |
| WO | 0078244 | * | 12/2000 | |

Primary Examiner—Gary K. Graham
(74) Attorney, Agent, or Firm—David A. Howley

(57) ABSTRACT

A head for a toothbrush including a neck and, first and second sets of one or more bristles each. The first and second sets are indirectly supported by the neck and movable relative to each other such that at least one component of this relative movement causes the bristle(s) of the first set to be raised and/or lowered relative to the bristle(s) in the second set. The first and second sets of bristles both are movable relative to the neck.

8 Claims, 8 Drawing Sheets

U.S. PATENT DOCUMENTS

| | | | | |
|---|---|---|---|---|
| 5,652,990 A | * | 8/1997 | Driesen | 15/28 |
| 5,709,233 A | * | 1/1998 | Boland et al. | 132/322 |
| 5,715,556 A | * | 2/1998 | Chung | 15/22.1 |
| 5,727,273 A | | 3/1998 | Pai | 15/22.1 |
| 5,732,433 A | * | 3/1998 | Gocking et al. | 15/28 |
| 5,738,575 A | * | 4/1998 | Bock | 433/216 |
| 5,769,102 A | | 6/1998 | Zebuhr | 132/322 |
| 5,778,474 A | * | 7/1998 | Shek | 15/22.1 |
| 5,836,030 A | * | 11/1998 | Hazeu et al. | 15/22.1 |
| 5,839,148 A | * | 11/1998 | Volpenhein | 15/167.1 |
| 5,842,245 A | | 12/1998 | Pai | 15/22.1 |
| 5,974,615 A | * | 11/1999 | Schwarz-Hartmann et al. | 15/22.4 |
| 6,032,313 A | * | 3/2000 | Tsang | 15/22.1 |
| 6,106,290 A | * | 8/2000 | Weissman | 433/122 |
| 6,148,462 A | | 11/2000 | Zseng | 15/22.1 |
| 6,209,164 B1 | | 4/2001 | Sato | 15/167.2 |
| 6,237,178 B1 | | 5/2001 | Krammer et al. | 15/22.1 |
| 6,338,176 B1 | | 1/2002 | Smith et al. | 15/28 |
| 6,349,442 B1 | | 2/2002 | Cohen et al. | 15/22.1 |
| 6,574,820 B1 | * | 6/2003 | DePuydt et al. | 15/28 |
| 2001/0001334 A1 | | 5/2001 | Gruber et al. | 15/22.1 |

\* cited by examiner

US 6,760,946 B2

BRUSH HEAD FOR TOOTHBRUSH

This application is a continuation of U.S. patent application Ser. No. 09/425,423 filed Oct. 22, 1999 now U.S. Pat. No. 6,574,820.

FIELD OF THE INVENTION

The invention relates generally to the field of oral care, and in particular to toothbrushes. More specifically, the invention relates to a brush head for a toothbrush.

BACKGROUND OF THE INVENTION

U.S. Pat. No. 5,577,285 (the '285 patent) discloses an electric toothbrush with a rotary bristle supporting structure. In one embodiment of the invention shown in FIG. 6, the brush head is driven such that an outer ring of bristles 45a and an inner ring of bristles 45b are moved in an alternating rotary motion in opposite directions. While such an arrangement is beneficial for cleaning, for example, the bucal or lingual tooth surfaces, the lack of motion of any of the bristles in an up and down pattern results in a less than optimal cleaning of the inter-dental tooth surfaces.

FIG. 9 of the '285 patent discloses an additional embodiment of the invention in which all of the bristles 45 are rotated about an axis 54 while also being moved in an up and down motion parallel to this axis. This embodiment will provide enhanced cleaning of the inter-dental tooth surfaces. However, the fact that all of the bristles are moved up and down limits the depth of penetration that the bristles can obtain between the teeth. This is because while some of the bristles are trying to penetrate between the teeth, others are pressing against, for example, the bucal tooth surface, thus limiting the motion of the brush head towards the teeth.

SUMMARY OF THE INVENTION

The present invention is directed to overcoming one or more of the problems set forth above. Briefly summarized, according to one aspect of the present invention, a head for an electric toothbrush includes a neck, a drive rod. and first and second sets of one or more bristles each. The first and second sets of bristles being respectively secured to first and second members. The first and second sets being indirectly supported by the neck and movable relative to each other. The second set of bristles being oscillatable about an axis. At least portions of the bristles of the first set are alternatingly movable directly towards and away from the axis through substantially the entire range of motion of the first set of bristles. The drive rod is directly coupled to the first and second members such that movement of the drive rod moves the first and second members to move the first and second sets of bristles.

According to another aspect of the invention, an electric toothbrush includes a head having a neck and first and second sets of one or more bristles each. The first and second sets of bristles are respectively secured to first and second members. The first and second sets are indirectly supported by the neck and movable relative to each other. The second set of bristles is oscillatable about an axis. At least portions of the bristles of the first set arc alternatingly movable directly towards or away from the axis through substantially the entire range of motion of the first set of bristles. A drive rod is directly coupled to the first and second members such that movement of the drive rod moves the first and second members to move the first and second sets of bristles.

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE INVENTION

Figure 1:
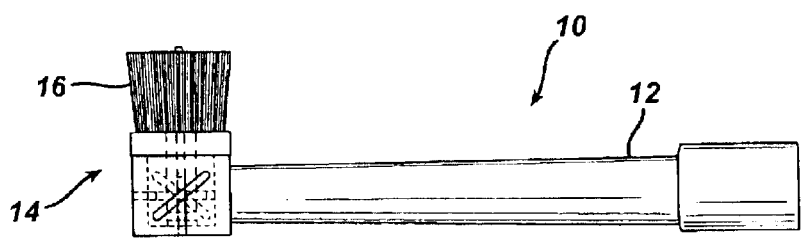
FIG. 1 is a side view of an electric toothbrush head attached to a brush handle/drive.

Beginning with FIG. 1, an electric toothbrush head 10 includes a neck 12 which is connected to a bristle support 14. Bristles 16 on support 14 are oscillated in a rotary movement through an arc of between about ±15 to 90 degrees, more preferably ±20 to 50 degrees as in a conventional electric toothbrush.

Figure 2:
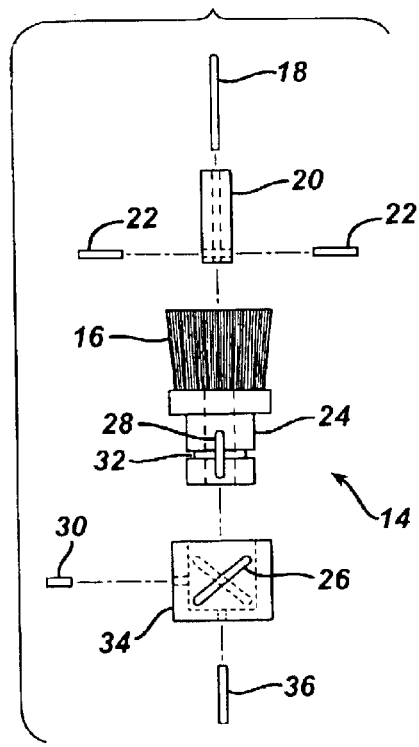
FIG. 2 is an exploded side view of the toothbrush head.

FIG. 2 shows support 14 in an exploded side view. An interdental probe 18 is secured to a slider core 20 in the center of bristles 16. Probe 18 can be a single large bristle or a tuft of much smaller bristles. Alternatively, core 20 can be enlarged to accommodate a plurality of probes (not shown), one of which may be positioned in the center of the core (as in FIG. 1), with the remainder of the probes being positioned on the core away from its center.

A pair of cam follower pins 22 are secured to opposite sides of the lower portion of core 20. Core 20 is positioned inside of a brush base 24 such that pins 22 are forced to ride along respective cam tracks 26 as well as respective vertical slider tracks 28 (one slider track is hidden behind the other). A retaining pin 30 rides in a track 32 to retain base 24 within a housing 34. A guide/rotation pin 36 passes through a hole in the bottom of housing 34 and is secured to base 24.

Figure 3A:
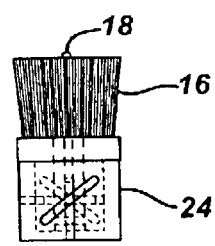
FIG. 3A is a side view of the head with a central bristle in a retracted position.
Figure 3B:
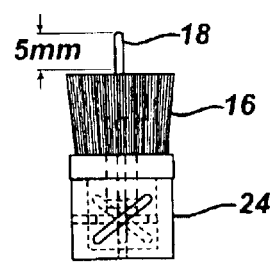
FIG. 3B is a side view of the head with a central bristle in an extended position.

Operation of support 14 will be explained with reference to FIGS. 2, 3A and 3B. Pin 36 is oscillated about its long axis by a drive mechanism (not shown) in neck 12. The drive mechanism can be of conventional design. Oscillation of pin 36 causes brush base 24 and bristles 16 to oscillate in a rotary pattern. Pin 30 retains base 24 within housing 34. Oscillation of base 24 causes core 20 and probe 18 to oscillate with the base because pins 22 ride in track 28 of the base. Pins 22 also ride in respective tracks 26 in the housing, thus causing core 20 and probe 18 to move up and down relative to bristles 16 during oscillation of brush base 24. FIGS. 3A and 3B show that a preferred extension of probe 18 from its lowest to highest position is about 5 mm.

In an alternative embodiment, all of bristles 16 are eliminated, leaving only probe 18 for cleaning teeth. This embodiment would be used primarily for cleaning interdental spaces, not for cleaning the other surfaces of teeth.

Turning to FIGS. 4–7, a second embodiment of the invention will be described. A brushead 40 can be attached to a handpiece (not shown) of an electric toothbrush. A driveshaft (not shown) protrudes out of the handpiece and can effect an oscillating rotation. Brushhead 40 includes a tube 42 in which a shaft 44 is located. The rear end of tube 42 fits into the housing (not shown) of the handpiece. Shaft 44 engages the driveshaft of the handpiece. A pin 46 is press fitted into shaft 44. Pin 46 can rotate at its free end in a bearing hole 48 in a front part 50 of tube 42. Axis 52 of pin 46 coincides with the axis of the driveshaft of the handpiece.

A pivot 54 can rotate in a bearing hole 56 situated in front part 50 of tube 42. Pivot 54 is retained in hole 56 by a ring 58. A brush base 60 is press fitted onto pivot 54. Brush base 60 has holes 62 in which tufts of bristles 64 are secured. A cross pin 66 is welded onto the free end of pivot 54. Both ends of cross pin 66 retain brush base 60 on pivot 54 by interaction with a shoulder 68 of the brush base. The central part of cross pin 66 is placed in a bearing hole 70 of a rocker 72. Rocker 72 can swivel about cross pin 66 and contains holes 74 in which tufts of bristles 76 are secured.

Shaft 44 includes a bearing hole 78 in which a drive rod 80 can move. The distance between axis 52 of pin 46 and an axis 82 of drive rod 80 is a radius r1. A stud 84 is welded onto the free end of drive rod 80. The distance between an axis 86 of pivot 54 and an axis 88 of stud 84 is a radius r2. Stud 84 can move in a bearing seat 90 in brush base 60. At one end of stud 84 is carried a ball 92 which can move in a cylindrical slot 94 in rocker 72.

When shaft 44 is oscillated about axis 52 through an angle of ± alpha 1 about pin 46, two different motions are induced. First, brush base 60 and rocker 72 are oscillated in a rotating manner through an angle of ± beta 1 about pivot 54 in bearing hole 56. This oscillating rotation causes bristles 64 to wipe plaque off teeth like a broom. Second, rocker 72 is oscillated in a rotating manner through an angle of ± gamma 1 about cross pin 66 in bearing hole 70. Oscillation of rocker 72 about pin 66 causes bristle tufts 76 to loosen plaque like a chisel. Two cycles of oscillation of rocker 72 about pin 66 occur for every one cycle of oscillation of base 60 and rocker 72 about pivot 54. The relations between the oscillation angles alpha 1 to beta 1 and alpha 1 to gamma 1 depend only on radii r1 and r2.

Referring to FIGS. 8–12, a third embodiment of the invention will be described. The third embodiment modifies the relationship between the oscillation angles, primarily to increase the gamma angle of the oscillating rotation of rocker 72. The basic features of the third embodiment remain unchanged from the second embodiment. The main difference is in the location of the drive rod.

In the mid-position of the oscillating rotation of a shaft 100, a drive rod 102 is located at a distance e from a median plane 104 of a brushhead 106. A stud 108 is welded laterally on a free end of drive rod 102 with a distance e between the centerlines. Stud 108 is movable in a bearing seal 110 of a brush base 112. When a drive shaft 114 is in a mid-oscillation position, stud 108 is in a median plane 116 of brush base 112. Drive rod 102 can move in a bearing hole 118 in shaft 114. Bearing hole 118 is situated in the distance e from median plane 104 of shaft 114 when the shaft is in its mid-oscillation position.

When shaft 114 is oscillated about median plane 104 through an angle of ± alpha 1, two different motions are induced. First, brush base 112 and rocker 72 are oscillated in a rotating manner through an angle of ± beta 2 which is smaller than ± beta 1 about axis 120. Second, rocker 72 is oscillated in a rotating manner through an angle of ± gamma 2 which is bigger than ± gamma 1 about cross pin 66. The relations between the oscillation angles alpha 1 to beta 2 and alpha 1 to gamma 2 depend on radii r1 and r2 as well as on the distance e.

In embodiments 2 and 3 of the invention, one component of the rocking motion of rocker 72 causes bristles 76 to move up and down (i.e. substantially parallel to pivot 54) relative to bristles 64.

Figure 4:
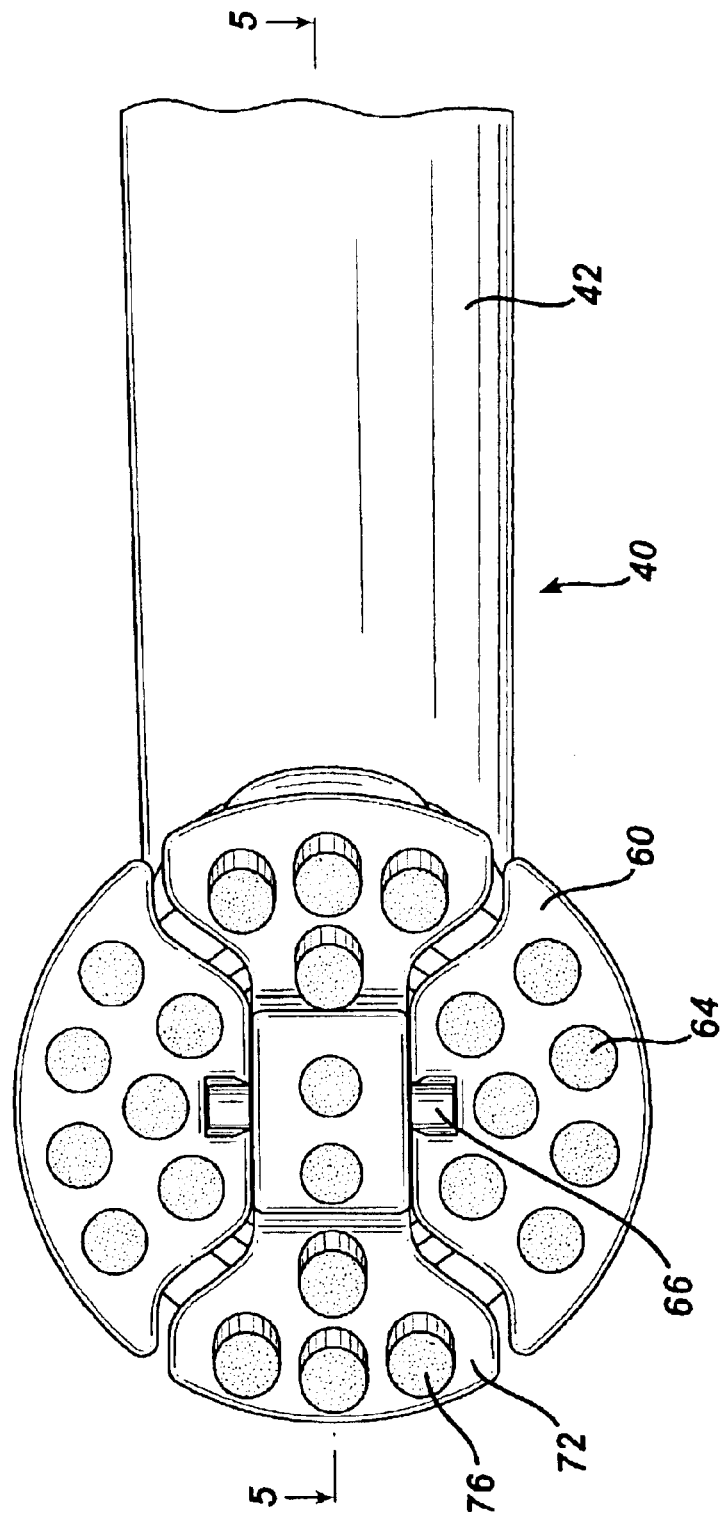
FIG. 4 is a top plan view of a second embodiment of an electric toothbrush head.
Figure 5:
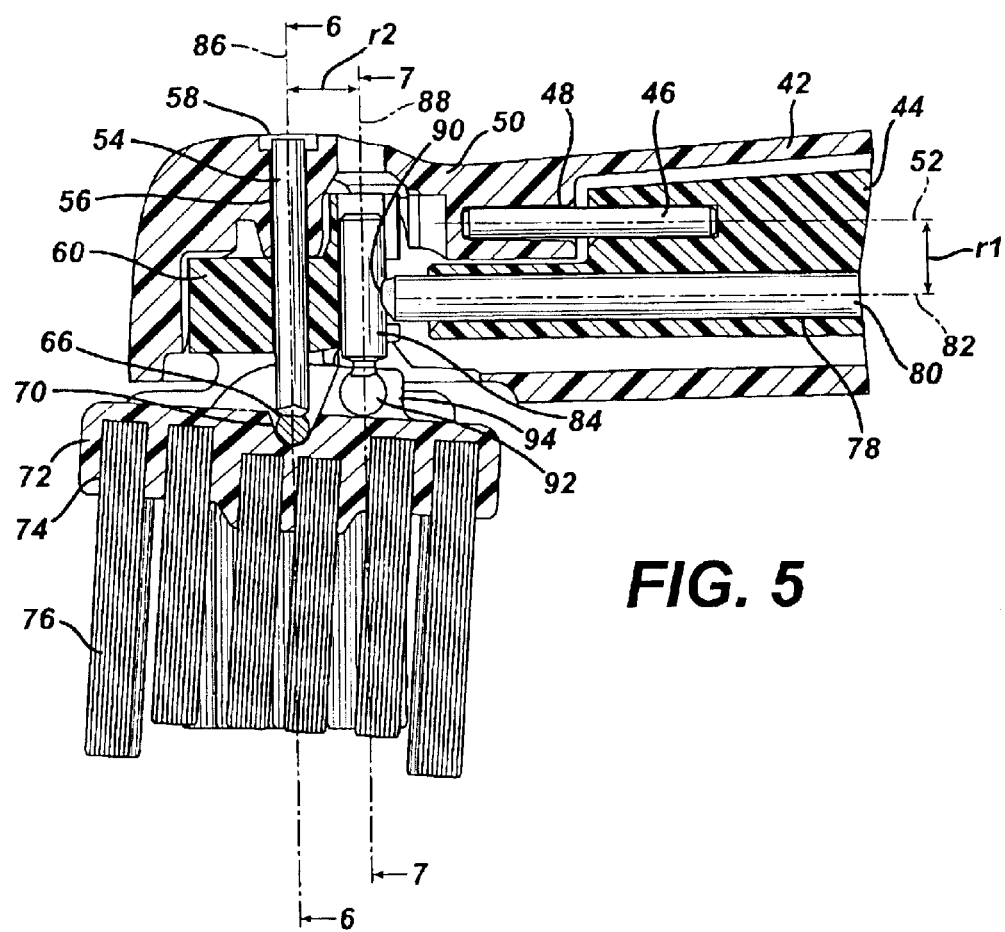
FIG. 5 is a sectional view of FIG. 4 taken along the lines 5—5.
Figure 6:
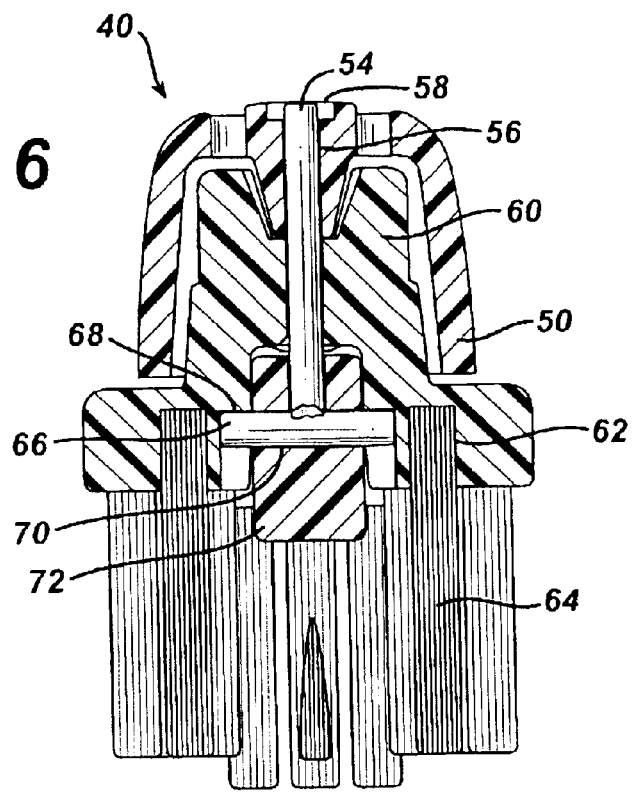
FIG. 6 is a sectional view of FIG. 5 taken along the lines 6—6.
Figure 7:
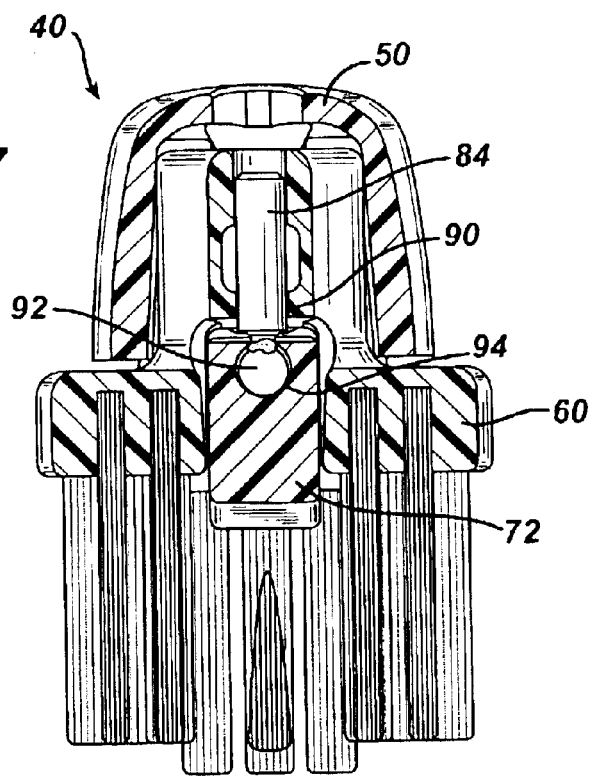
FIG. 7 is a sectional view of FIG. 5 taken along the lines 7—7.
Figure 8:
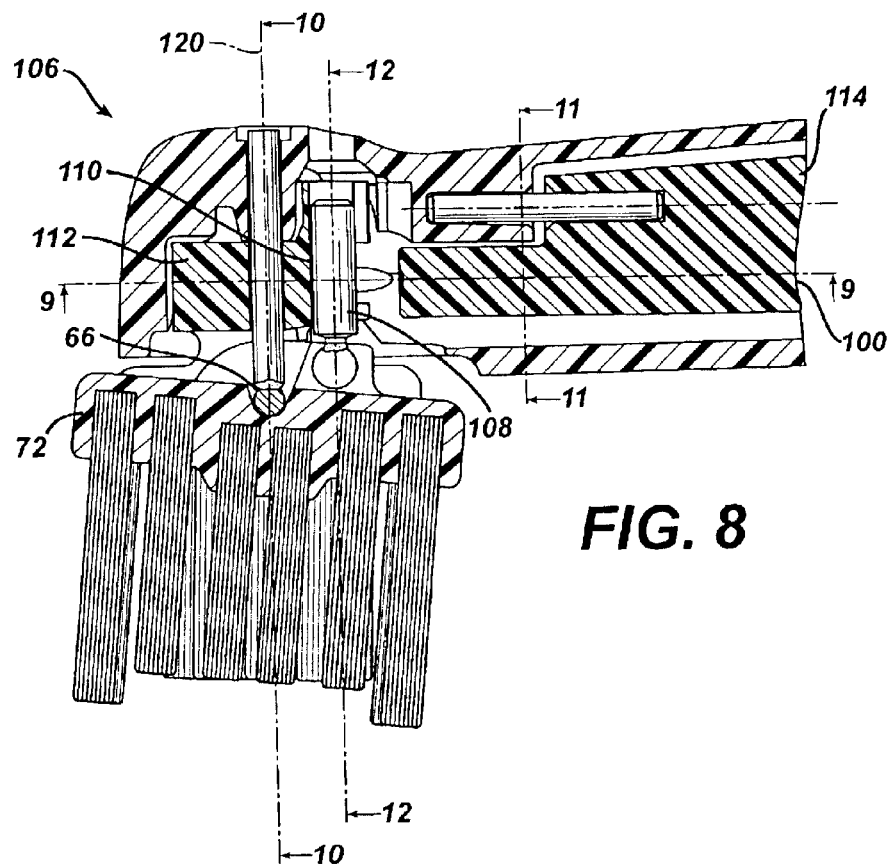
FIG. 8 is a sectional view similar to FIG. 5 of a third embodiment of the invention.
Figure 9:
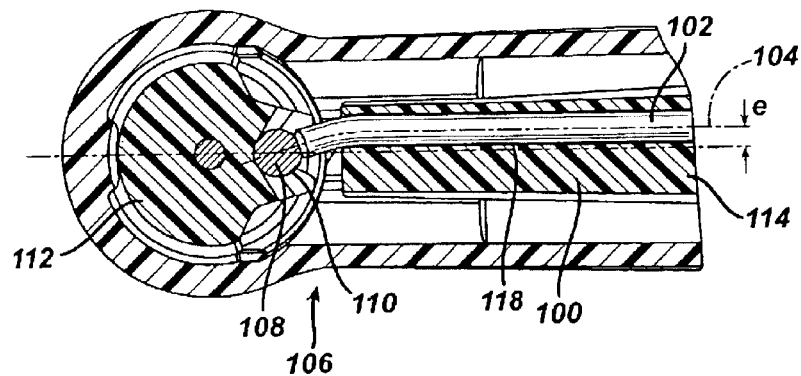
FIG. 9 is a sectional view of FIG. 8 taken along the lines 9—9.
Figure 10:
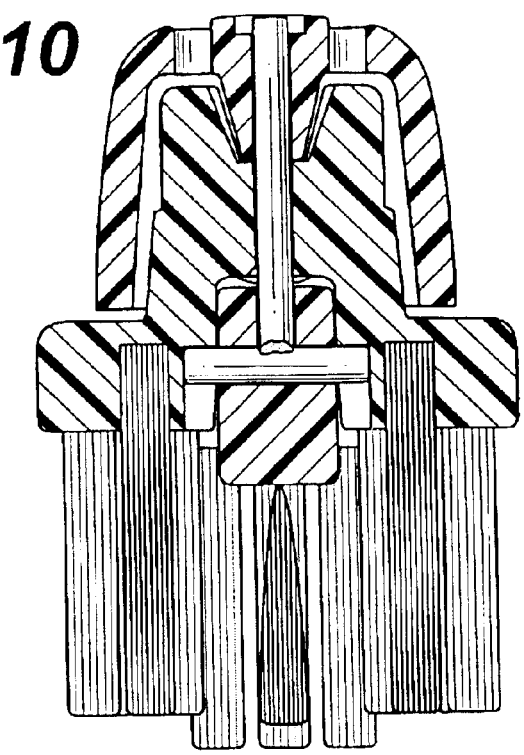
FIG. 10 is a sectional view of FIG. 8 taken along the lines 10—10.
Figure 11:
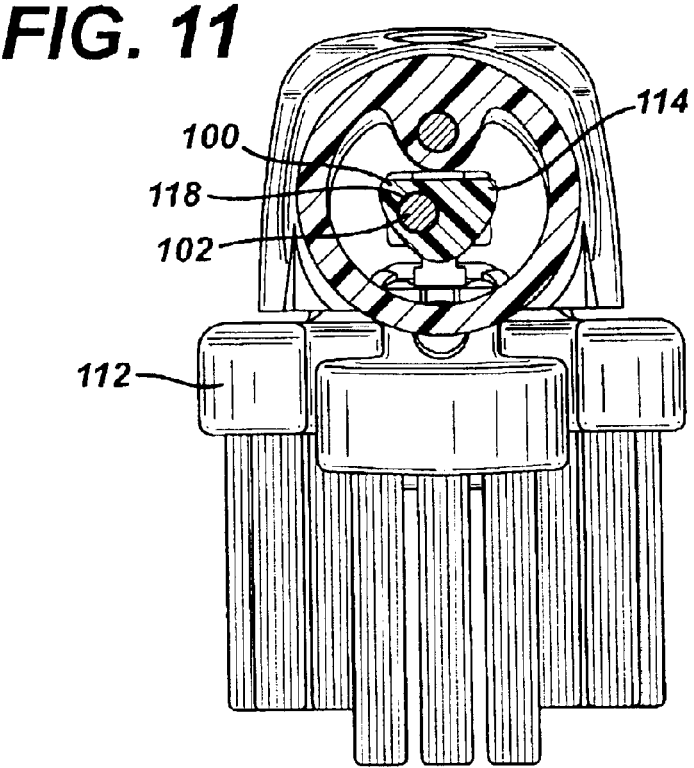
FIG. 11 is a sectional view of FIG. 8 taken along the lines 11—11.
Figure 12:
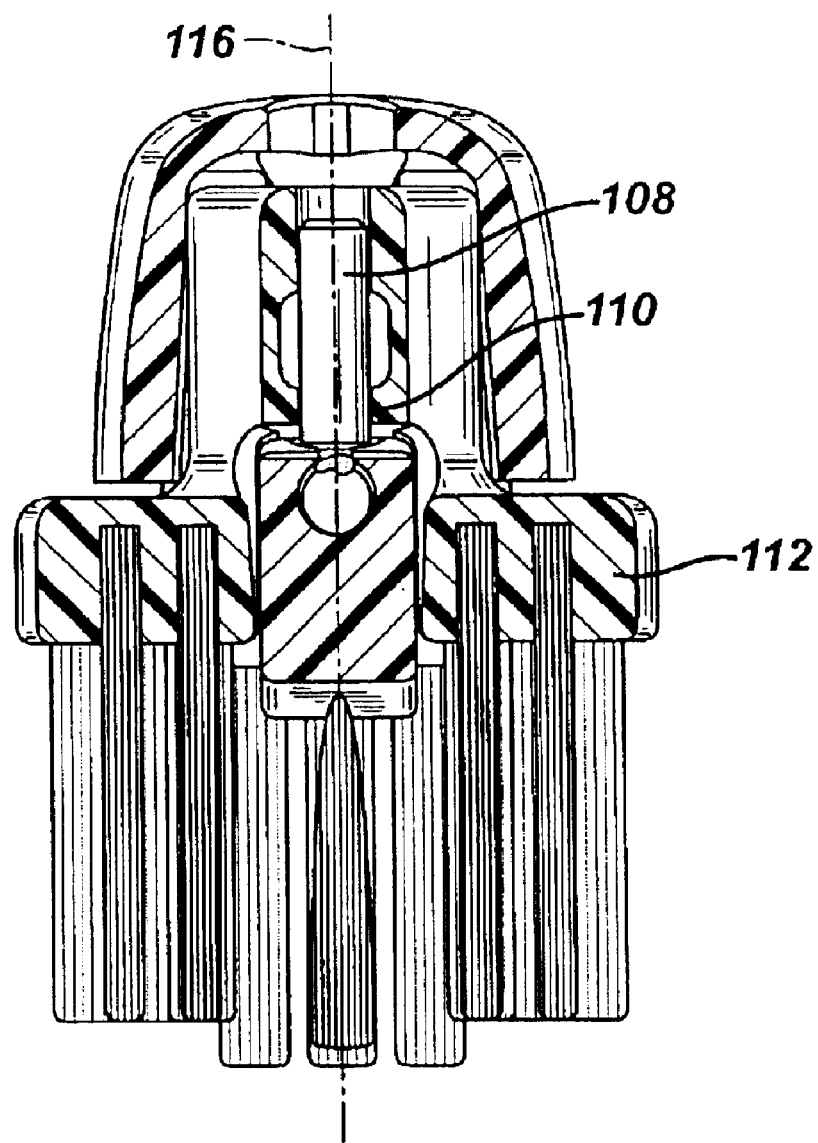
FIG. 12 is a sectional view of FIG. 8 taken along the lines 12—12.
Figure 13:
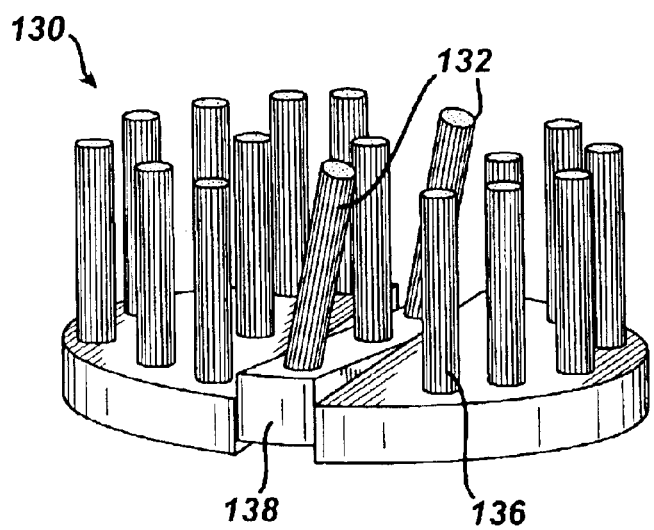
FIG. 13 is a perspective view of a fourth embodiment of a toothbrush head.
Figure 14:
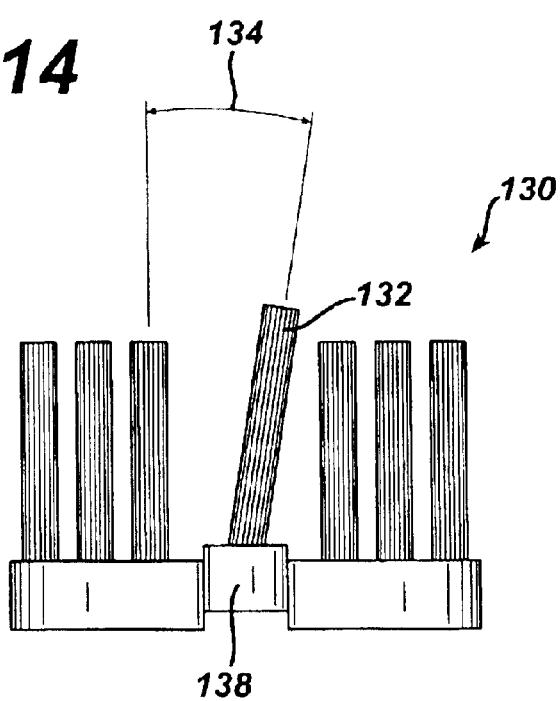
FIG. 14 is a front view of the toothbrush head of FIG. 13.

FIGS. 13 and 14 disclose a toothbrush head 130 which is similar in function to the head of FIG. 4. The major difference is that tufts of bristles 132 are tilted away from the perpendicular (to the top surface of a pivot bar 138) at an angle 134 of between about 1–20 degrees. Preferably the bristles are tilted along the direction of oscillation of bristles 136. Such tilting of bristles 132 provides better interdental penetration during the respective upstrokes of pivot bar 138, particularly for the tuft(s) on bar 138 which are being moved by head 138 in the tilt direction. It is preferable that tufts of bristles on both sides of bar 138 have the same tilt angle and are tilted in the same direction (i.e. in the same plane). Alternatively, tufts of bristles on opposite sides of the bar can be tilted in opposite directions.

The invention has been described with reference to several embodiments including a preferred embodiment. However, it will be appreciated that variations and modifications can be effected by a person of ordinary skill in the art without departing from the scope of the invention.

What is claimed is:

1. A head for an electric toothbrush, comprising:
a neck;
a drive rod; and
first and second sets of one or more bristles each, the first and second sets of bristles being respectively secured to first and second members, the first and second sets being indirectly supported by the neck and movable relative to each other, the second set of bristles being oscillatable about an axis, at least portions of the bristles of the first set being alternatingly movable directly towards and away from the axis through substantially the entire range of motion of the first set of bristles, the drive rod being directly coupled to the first and second members such that movement of the drive rod moves the first and second members to move the first and second sets of bristles.

2. The head of claim 1, wherein the first and second sets of bristles are movable relative to the neck.

3. The head of claim 1, wherein the drive rod is oscillateable.

4. The head of claim 3, wherein the drive rod is oscillateable about an axis.

5. An electric toothbrush, comprising:
a head having a neck;
first and second sets of one or more bristles each, the first and second sets of bristles being respectively secured to first and second members, the first and second sets being indirectly supported by the neck and movable relative to each other, the second set of bristles being oscillatable about an axis, at least portions of the bristles of the first set being alternatingly movable directly towards or away from the axis through substantially the entire range of motion of the first set of bristles; and a drive rod, the drive rod being directly coupled to the first and second members such that movement of the drive rod moves the first and second members to move the first and second sets of bristles.

6. The toothbrush of claim 5, wherein the first and second sets of bristles are movable relative to the neck.

7. The toothbrush of claim 3, wherein the drive rod is oscillateable.

8. The toothbrush of claim 7, wherein the drive rod is oscillateable about an axis.

* * * * *